United States Patent [19]
Eager et al.

[11] Patent Number: 5,908,433
[45] Date of Patent: *Jun. 1, 1999

[54] CARPAL TUNNEL KNIFE

[75] Inventors: Kris D. Eager, Richland, Mich.;
William E. Nordt, III, Richmond, Va.;
Douglas L. Tyler, Sr., Paw Paw, Mich.

[73] Assignee: Stryker Corporation, Kalamazoo, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/644,855

[22] Filed: May 10, 1996

[51] Int. Cl.$^6$ ...................................................... A61B 17/32
[52] U.S. Cl. ............................................ 606/170; 263/119
[58] Field of Search ..................................... 606/170, 167, 606/169, 159, 166, 172; 263/119, 120

[56] References Cited

U.S. PATENT DOCUMENTS

| | | |
|---|---|---|
| 117,588 | 8/1871 | Woods . |
| 191,569 | 6/1877 | Clark . |
| 208,459 | 10/1878 | Budlong . |
| 557,887 | 4/1896 | Robertson . |
| 936,474 | 10/1909 | Post . |
| 940,857 | 11/1909 | Cumms . |
| 989,255 | 4/1911 | Hasselmann . |
| 1,099,885 | 6/1914 | Peple . |
| 1,131,141 | 3/1915 | Kalenborn . |
| 2,610,399 | 9/1952 | Adams et al. . |
| 2,705,833 | 4/1955 | Grantz . |
| 2,764,814 | 10/1956 | Jecker . |
| 3,028,670 | 4/1962 | Tilly . |
| 3,230,620 | 1/1966 | Embleton . |
| 3,365,798 | 1/1968 | Cunningham . |
| 3,486,228 | 12/1969 | James . |
| 3,751,806 | 8/1973 | Patrick . |
| 3,831,274 | 8/1974 | Horrocks . |
| 3,890,960 | 6/1975 | Wunsch nee Kuhn et al. . |
| 3,972,117 | 8/1976 | Fogg . |
| 3,975,822 | 8/1976 | Mabus . |
| 4,026,295 | 5/1977 | Lieberman ............................. 606/170 |
| 4,081,907 | 4/1978 | Bosshold . |
| 4,604,804 | 8/1986 | Sparks . |

(List continued on next page.)

FOREIGN PATENT DOCUMENTS

| | | |
|---|---|---|
| 24 131 | 12/1882 | Germany . |
| 38 26 786 A1 | 2/1990 | Germany . |
| 1 463 249 | 3/1989 | Russian Federation . |
| 2 247 | 1/1890 | United Kingdom . |
| 12 354 | 1/1892 | United Kingdom . |
| 603 942 | 6/1948 | United Kingdom . |
| 2 203 341 | 10/1988 | United Kingdom . |

OTHER PUBLICATIONS

Erichsen Arthroscopic Instruments, Stryker Corporation, one page.
Hydraulic Operating Stool, Stryker Corporation, 1969, one page.
Cordotomy Knives—order direct from Ruggles Corporation (1 page).
Bilateral Carpal Tunnel Release at One Operation: Report of 228 Patients, Pagnanelli and Barrer, Neuosurgery, vol. 31, No. 6 (5 page ).
Carpal Tunnel Syndrome, Decompression Using the Paine Retinaculotome, Paine and Polyzoidis (6 page).
Carpal Tunnel Syndrome: Surgical Treatment Using The Paine Retinaculatome, Pagnaneli and Barrer, J. Neurosurg/vol. 75 (6 page).

*Primary Examiner*—Michael Buiz
*Assistant Examiner*—Kevin Truong
*Attorney, Agent, or Firm*—Flynn, Thiel, Boutell & Tanis, P.C.

[57] ABSTRACT

A surgical knife for carpal tunnel surgeries having a housing with an adjacent light source and a light transmitting blade holder transmitting the light from the housing around the blade. The light illuminates the surgical site and assists the surgeon in precisely locating the cutting blade.

11 Claims, 3 Drawing Sheets

U.S. PATENT DOCUMENTS

| | | |
|---|---|---|
| 4,962,770 | 10/1990 | Agee et al. . |
| 4,963,147 | 10/1990 | Agee et al. . |
| 5,029,573 | 7/1991 | Chow . |
| 5,046,253 | 9/1991 | Ireland . |
| 5,219,350 | 6/1993 | Emerson et al. ......................... 362/119 |
| 5,273,024 | 12/1993 | Menon et al. . |
| 5,323,765 | 6/1994 | Brown . |
| 5,341,822 | 8/1994 | Farr et al. . |
| 5,346,503 | 9/1994 | Chow . |
| 5,356,419 | 10/1994 | Chow . |
| 5,387,222 | 2/1995 | Strickland . |
| 5,387,223 | 2/1995 | Agee et al. . |
| 5,413,580 | 5/1995 | Stephenson . |
| 5,507,800 | 4/1996 | Strickland . |
| 5,569,300 | 10/1996 | Redmon . |
| 5,577,829 | 11/1996 | Hall ......................................... 362/119 |
| 5,578,051 | 11/1996 | Mirza . |
| 5,584,565 | 12/1996 | Berg . |

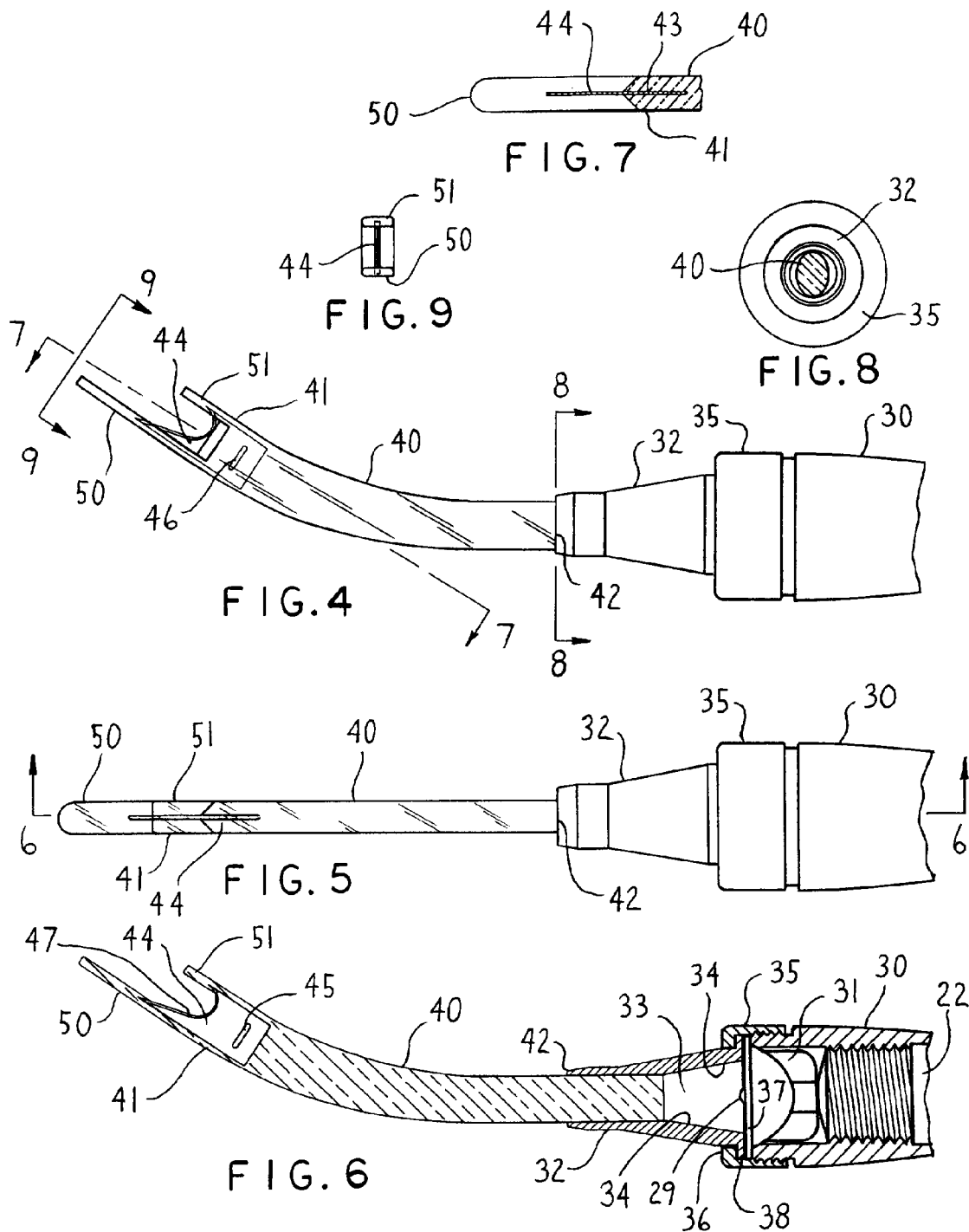

CARPAL TUNNEL KNIFE

FIELD OF THE INVENTION

This invention relates to a surgical knife, particularly suited for carpal tunnel release surgeries.

BACKGROUND OF THE INVENTION

Known carpal tunnel knives have a handle with a blade holder. The blade holder has two finger-like prongs extending forwardly above and below the blade. An example of this type of surgical knife is found in U.S. Pat. No. 5,387,222 issued to Strickland.

The prongs extend beyond the blade and straddle the targeted tissue to be cut. The prongs assist in guiding the blade only through the targeted carpal ligament during carpal tunnel release surgery. One prong may be longer than the other, with the longer prong guided below the carpal ligament in an attempt to protect the median nerve and other tissues from unwanted damage.

The surgical blade is positioned between the two prongs and is wide enough to cut the entire thickness of the targeted tissue, but not endanger surrounding tissue. A common width is 3 mm, which roughly corresponds to the thickness of most adults' carpal tunnel ligaments.

However, with the known carpal tunnel knives inserted into the patient's hand, it is still difficult to locate the exact position of the instrument and its cutting blade. Surgeons must still locate the instrument in the patient's hand by feel, mainly by the resistance experienced by the cutting blade and the distance the knife is inserted into the patient's hand. While the knife is inserted, it obstructs light entry into the surgical wound thus interfering with the surgeons ability to see the surgical site.

SUMMARY OF THE INVENTION

A surgical knife for carpal tunnel release surgery having a handle and a blade holder attached to the handle. The blade holder is of light transmitting material to provide light at the surgical site from a light source adjacent the handle.

BRIEF DESCRIPTION OF THE DRAWINGS

FIG. 4 is a side view of the FIG. 1 knife.

FIG. 5 is a top view of the FIG. 1 knife.

FIG. 6 is a central cross-sectional view taken substantially along line 6—6 in FIG. 5.

FIG. 7 is a fragmentary cross-sectional view taken substantially along line 7—7 in FIG. 6.

FIG. 8 is a sectional view taken substantially along line 8—8 in FIG. 4.

FIG. 9 is a sectional view taken substantially along line 9—9 in FIG. 4.

DETAILED DESCRIPTION

Figure 1:
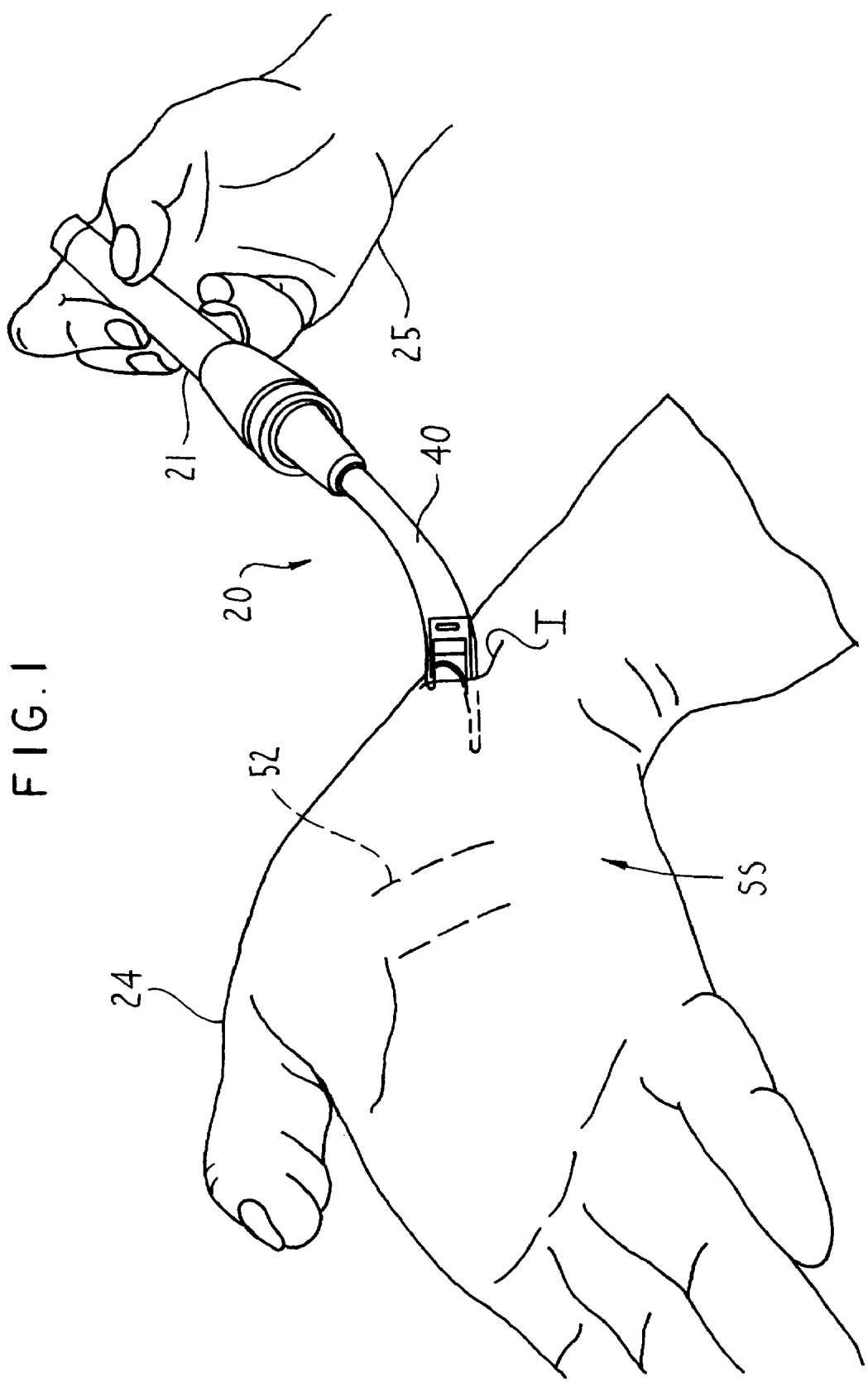
FIG. 1 is a pictorial view showing a surgical knife embodying the invention and in surgical use.
Figure 2:
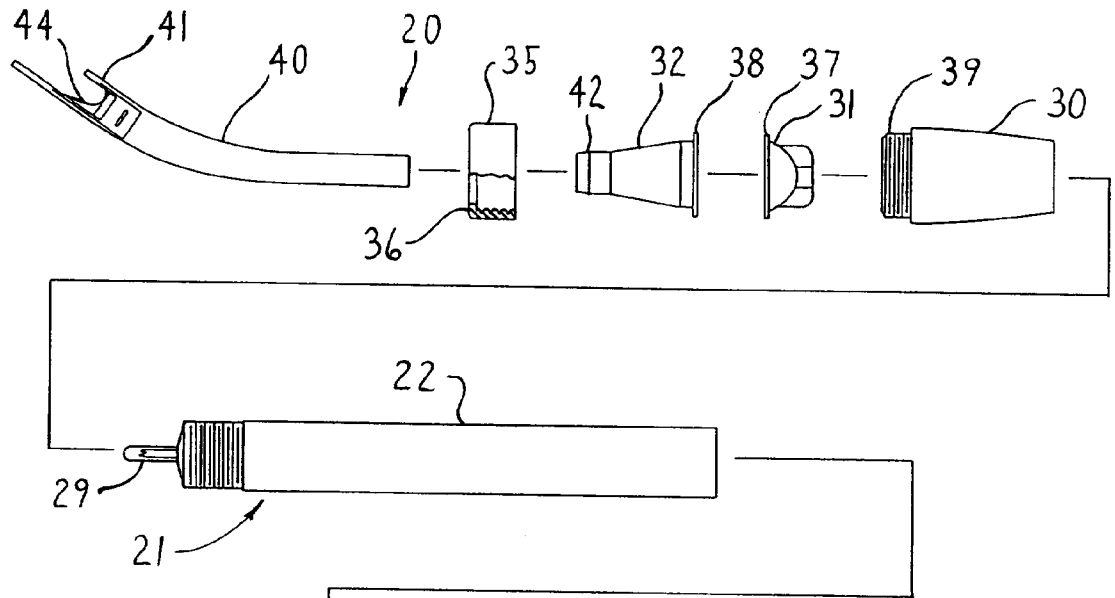
FIG. 2 is a schematic exploded view of the FIG. 1 knife.
Figure 2A:
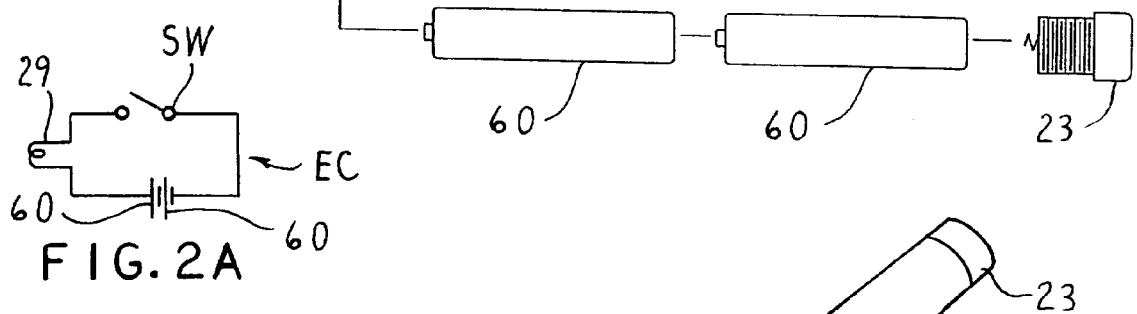
FIG. 2A is an electrical schematic of the FIG. 1 knife.
Figure 3:
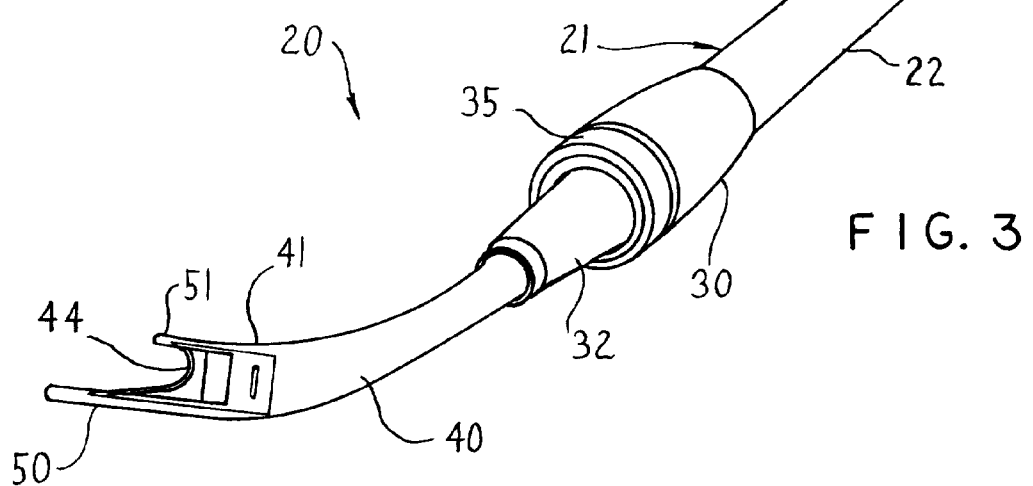
FIG. 3 is a pictorial view of the FIG. 1 knife.

A surgical knife 20 (FIG. 1), embodying the invention, has a handle 21 for gripping by the hand 25 of a surgeon, e.g. for surgery on the hand 24 of the patient. The handle 21 (FIG. 2) includes a hollow tubular housing 22. A suitable electric power source, here batteries 60, e.g. conventional AA batteries, is located in the housing 22. A cap 23 closes the rear end of the housing 22. A light source, such as a bulb 29, is located on the front end of the handle 21, opposite the cap 29. The handle 21 includes a hollow end opening lamp head 30 fixed (here threaded) around the bulb 29 on the front end of the battery housing 22. A light reflector 31 in the head 30 surrounds the bulb 29 and is housed in the lamp head 30. The handle 21 includes an electric switch SW (indicated schematically in FIG. 2A) of any known type movably actuable to complete an electric circuit EC, through the series batteries 60 and light bulb 29, to illuminate the bulb.

An internally threaded retainer ring 35 is fixed threadedly on corresponding external threads 39 on the lamp head 30. The threaded ring 35 has a front, interior flange 36 which clamps the light reflector 31 snugly on the lamp head 30 as further discussed below. The handle portion of the carpal tunnel knife 20, to the extent discussed above was implemented in one unit embodying the invention, by using a commercially available described above, hand-held flashlight sold widely in stores under the trademark MINI MAGLIGHT® by Mag Instruments of California, but with the usual lens missing. To the extent above described,, the knife 20 may thus be conventional. Other constructions for the handle portion 21-31 and 35, 39 are, however, contemplated.

Turning now toward aspects more specific to this invention a hollow funnel-like adaptor 32 (FIG. 6) fixedly, forwardly extends from the lamp head 30. The light from the bulb 29 passes forward through the hollow interior 33 of the adaptor 32. The adaptor 32 is of an opaque, rigid material, hereof anodized aluminum with a polished inner surface 34, although alternatively a molded plastics material is contemplated. The polished inner surface 34 assists such passage of the light by reflecting, and not absorbing, most of the light energy.

The reflector 31 and adaptor 32 have radially outward extending flanges 37 and 38 clamped by the ring flange 36 (FIG. 6) fixedly against the front end of the housing 22, to affix the adaptor 32 to the handle 21.

A blade holder 40 (FIGS. 4–6) is fixedly inserted into the narrow end 42 of the funnel shaped adaptor 32. The blade holder 40 is preferably adhesively bonded in the narrow front end of the adaptor 32. The blade holder 40 is of rigid, light transmitting material, such as transparent plastic material. The blade holder 40 transmits light endwise, from the turned on bulb 29 through the narrow end 42 of the adaptor 32 forward to the front end portion 41 of the blade holder 40, and laterally around the blade holder. The illumination provided by the front end portion 41 of the blade holder 40 will illuminate tissue forwardly and around the front end portion 41 of the blade holder, thereby allowing the surgeon to visually locate the position of the front end portion 41. With sufficient light brightness, the surgeon will be able to locate the front end portion 41 of the knife 20 even after it is inserted in the patient's hand 24.

The blade holder 40 is curved to allow the surgeon to easily insert it into an incision I (FIG. 1) in the patient's hand and to follow the natural rotation of the surgeon's hand during entry into the surgical site SS. The blade holder 40 preferably is oval in cross-section to minimize the width of the blade holder while still being able to hold a sufficiently tall blade (hereafter described at 44). The minimized width advantageously minimizes disruption of patient tissue during surgery and so reduces the patient's discomfort and recovery time.

A slot 43 (FIG. 7) in the front end portion 41 of the blade holder 40 receives the rear portion of a blade 44. The blade here has a concavely rounded, forward facing cutting edge 47. An aperture 45 is provided in the rear portion of the blade 44. A projection of the holder 40 crosses the slot 43 and fills the aperture 45 to fix the blade 44 in the slot 43.

A pair of prongs 50, 51 extend forward of the remainder of the front end portion 41 of the blade holder 40, along and beyond the top and bottom (FIG. 6) edges of the blade 44. In the preferred embodiment shown, prongs 50, 51 are relatively flat and rectangular in plan (FIG. 5). The ends are rounded to minimize trauma to the patient's hand. These prongs 50, 51 assist the surgeon in guiding the blade 44 to cut only the targeted carpal ligament 52 (FIG. 1) and can act as retractors. The prongs 50, 51 integrally extend forward the blade holder 40 and are of the same light transmitting material. As a result, the prongs illuminate patient tissue around and forward of the blade 44 and can shine light through the overlying skin, to further assist the surgeon in precisely locating the blade 44 with respect to internal hand tissue of interest.

The bottom prong 50 is longer than the top prong 51. This assists the surgeon in guiding the blade 44 only along the targeted tissue, namely, the transverse carpal ligament 52 further avoiding unwanted tissue damage. The elongate bottom prong 50 extends beyond the blade 44 and thus illuminates tissue ahead of the blade 44 as the blade holder is advanced through the incision I toward the surgical site SS.

The shape of the blade cutting edge and prongs 50 and 51 here shown are, for convenience in illustration, similar to that shown in aforementioned Strickland U.S. Pat. No. 5,387,222, although other shapes are contemplated.

The holder 40 is preferably a unitary molded plastic piece and the blade rear end portion is fixed therein during holder molding operation.

Although a particular preferred embodiment of the invention has been disclosed in detail for illustrative purposes, it will be recognized that variations or modifications of the disclosed apparatus including the rearrangements and combination of parts, lie within the scope of the present invention.

The embodiments of the invention in which an exclusive property or privilege is claimed are defined as follows:

1. A carpal tunnel knife for illuminating and therewith helping a surgeon see the carpal ligament in the hand of a patient in advance of cutting such carpal ligament, and comprising:

a hand engageable light producing handle having a light source;

an elongate, light transmitting, blade holder fixedly extending substantially forwardly from said light producing handle and transmitting light forwardly therealong from said handle;

a carpal ligament cutting blade fixed on said light transmitting holder at a location spaced between the front and rear ends of said light transmitting holder, said blade having a front edge including a cutting portion spaced between said front and rear ends of said light transmitting holder;

said light transmitting blade holder including an elongate light emitting prong extending forward from one end of said front edge of said blade and therewith simultaneously contacting and illuminating a carpal ligament spaced ahead of said front blade edge in the hand of a patient, said elongate light emitting prong having a light emitting front end portion spaced ahead of said blade and therewith simultaneously contacting and illuminating an area of patient tissue adjacent a carpal ligament prior to contact of said carpal ligament by said blade, so as to avoid dependence on light emission behind the blade for illuminating patient tissue ahead of the blade in the surgical site and avoid interference with a surgeon's ability to see the surgical site with the carpal tunnel surgical knife inserted in a patient's hand.

2. The apparatus of claim 1 in which said blade holder is of rigid, light transmitting material capable of transmitting light forwardly endwise therein from said light producing handle, forwardly laterally around said blade, to the front end portion of said prong.

3. The apparatus of claim 2 in which said blade holder material is substantially transparent plastic material, said substantially transparent plastic material extending forward past the blade and defining said prong.

4. A tissue working surgical instrument, comprising:

a handle;

an electric power supply operatively associated with said handle;

a light source shining forward from said handle;

an electrical circuit for selectively supplying power from said electric power supply to said light source to thereby produce light;

a light transmitting blade holder extending from said handle for transmitting the light;

a blade positioned adjacent a front portion of said light transmitting blade holder, said front portion of said blade holder including a light transmitting prong extending forward from said blade and illuminating patient tissue ahead of said blade.

5. The surgical instrument of claim 4 in which said light transmitting prong is molded of substantially transparent plastics material.

6. The apparatus of claim 4 in which said light transmitting blade holder comprises a substantially transparent molded plastics element having light transmitting portions flanking sides of said blade and located intermediate the ends of said blade holder in spaced relation to said blade holder ends.

7. The apparatus of claim 6 in which said blade is planar.

8. The apparatus of claim 4 in which said light transmitting blade holder comprises a substantially transparent molded plastics element molded about portions of said blade excluding a forward facing cutting edge of said blade.

9. A tissue working surgical instrument, comprising:

a handle;

an electric power supply operatively associated with said handle;

a light source shining forward from said handle;

an electrical circuit for selectively supplying power from said electric power supply to said light source to thereby produce light;

a light transmitting blade holder extending from said handle for transmitting the light;

a blade positioned at a front portion of said light transmitting blade holder, said front portion of said blade holder including forward extending, light emitting prongs flanking opposite ends of a cutting edge of said blade and illuminating patient tissue ahead of said blade.

10. A method for carpal tunnel ligament release surgery, comprising the steps:

providing a carpal tunnel knife with a light producing handle, a light transmitting blade holder extending forward from and guiding light forward from said handle, and a blade fixed on said blade holder and spaced intermediate the ends of said blade holder, wherein said blade holder forward of said blade comprises a forward extending light emitting prong;

inserting said elongated light emitting prong into a surgical wound in the hand of a patient in a direction toward the carpal ligament;

illuminating, with said light emitting prong, patient tissue ahead of said blade while advancing said blade toward the carpal ligament and therewith (1) helping a surgeon visually locate the blade in the hand of the patient and (2) assisting the surgeon in guiding said blade only toward targeted tissue and avoiding unwanted tissue damage by the blade.

11. A tissue working surgical instrument, comprising:

an internally lighted blade holder, a blade secured in said blade holder, said blade having a blade edge for cutting patient tissue in a forward direction, and said blade holder having an internally lighted and light emitting protuberance, said protuberance extending forwardly beyond said blade edge to contact and illuminate tissue spaced forwardly ahead of said blade.

* * * * *